(12) United States Patent
Martin et al.

(10) Patent No.: US 8,942,440 B2
(45) Date of Patent: Jan. 27, 2015

(54) METHOD FOR GENERATING IMAGE FILES HAVING A NUMBER OF LOGICAL LAYERS

(75) Inventors: Diana Martin, Herzogenaurach (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 2119 days.

(21) Appl. No.: 12/010,026

(22) Filed: Jan. 18, 2008

(65) Prior Publication Data
US 2008/0181480 A1    Jul. 31, 2008

(30) Foreign Application Priority Data
Jan. 22, 2007    (DE) .......................... 10 2007 003 170

(51) Int. Cl.
*G06K 9/00*    (2006.01)
*G06F 19/00*    (2011.01)

(52) U.S. Cl.
CPC ............. *G06F 19/321* (2013.01); *Y10S 128/92* (2013.01); *Y10S 128/922* (2013.01)
USPC .............................. 382/128; 128/920; 128/922

(58) Field of Classification Search
USPC .......... 382/128, 129, 130, 131, 132; 128/920, 128/922
See application file for complete search history.

(56) References Cited

U.S. PATENT DOCUMENTS

| | | |
|---|---|---|
| 2003/0004405 A1 | 1/2003 | Townsend et al. |
| 2004/0071038 A1* | 4/2004 | Sterritt .......................... 365/232 |

* cited by examiner

*Primary Examiner* — Nicole Ippolito
(74) *Attorney, Agent, or Firm* — Harness, Dickey & Pierce, P.L.C.

(57) ABSTRACT

A method for image acquisition is disclosed. In an embodiment, the method includes acquiring, by a first imaging method, first image data of an object to be examined; acquiring, by a second imaging method, second image data of the object to be examined; generating an image file, the file format of which allows different logical layers of image data to be stored, in such a manner that the image file generated contains the acquired first image data in a first logical layer in the intended layer format and the acquired second image data in a second logical layer.

12 Claims, 1 Drawing Sheet

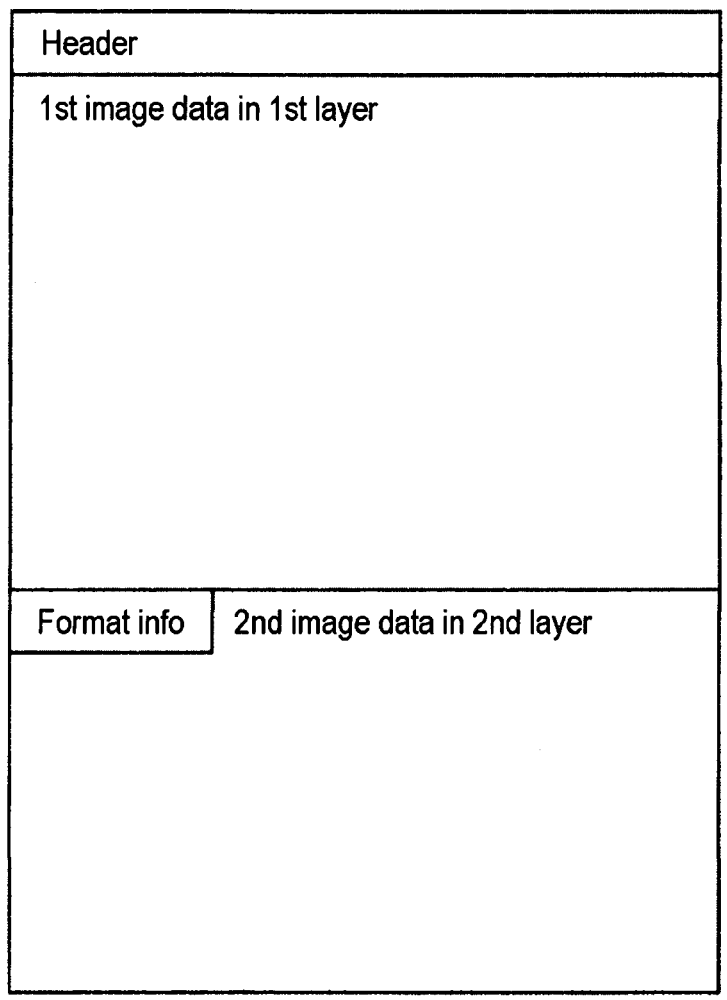

METHOD FOR GENERATING IMAGE FILES HAVING A NUMBER OF LOGICAL LAYERS

PRIORITY STATEMENT

The present application hereby claims priority under 35 U.S.C. §119 on German patent application number DE 10 2007 003 170.1 filed Jan. 22, 2007, the entire contents of which is hereby incorporated herein by reference.

FIELD

Embodiments of the present invention generally relate to a method for combining image data of different origin in logical layers of a single file.

BACKGROUND

In the field of medical imaging, so-called hybrid instruments are enjoying ever increasing popularity. A hybrid instrument in this context is understood to be device which is capable of simultaneously or immediately successively obtaining image information about a patient's body (or another object examined) by way of two different image acquisition technologies.

Examples of such hybrid instruments are hybrid PET (positron emission tomography)/CT (computed tomography) instruments which have almost completely replaced the conventional PET system, hybrid SPECT (single photon emission computed tomography)/CT instruments, and most recently hybrid MR (magnetic resonance)/SPECT instruments. Advantages of such hybrid instruments are that a method having a high spatial resolution (MR, CT) and a method having high sensitivity (SPECT, PET) synergistically complement one another.

In such hybrid instruments, the problem occurs that the standardized file formats for respective individual instruments are not optimally suitable for such hybrid modalities. During the examination, for example, an MR-PET produces both PT and MR data which are in each case processed separately and stored in separate files.

There are currently a number of methods and approaches for bypassing the above problem:
the shots are in each case stored as separate PET or MR images etc. It is advantageous in this context that the image records can be processed further with the existing programs, that is to say, for example, displayed, diagnostically examined, printed out or processed. However, this approach has the problem that the "image fusion" that is to say information about the correlation between the two (or more) image records produced is lost or the image records must be recombined in order to restore such image fusion if it is wanted or required.
the various records can be stored combined in a special file format. This can be selected in such a manner that amalgamated images can be optimally processed; but then the conformity with existing standards and file formats is lacking and processing can only take place in systems which can use the selected format.

SUMMARY

However, it would be desirable if the data obtained from the parts of the hybrid instruments could be uniformly acquired and if, nevertheless, the data could be processed with existing data processing systems. Thus, in at least one embodiment, the invention demonstrates an approach by which uniform data handling with hybrid instruments for imaging is possible.

Further advantageous embodiments, details and aspects of the present invention can be obtained from the description and the attached drawings.

The principle of at least one embodiment of the present invention resides in using an existing file format which allows a number of "layers" of image data to be stored in order to store the image information of the individual instruments in the various layers, but in the same file.

Accordingly, in a first aspect, an embodiment of the invention is directed to a method for image acquisition which has the following steps:
acquiring by way of a first imaging method first image data of an object to be examined;
acquiring by way of a second imaging method second image data of the object to be examined;
generating an image file, the file format of which allows different logical layers of image data to be stored in such a manner that the image file generated contains the acquired first image data in a first logical layer in the intended layer format and the acquired second image data in a second logical layer.

BRIEF DESCRIPTION OF THE DRAWINGS

The present method is explained briefly once again below with the aid of an example embodiment in conjunction with the drawings, without restricting the scope of protection prescribed by the patent claims, wherein:

FIG. 1 shows, in a greatly diagrammatic representation, a file with image information which has been generated in accordance with the method of an embodiment of the present invention and, respectively, by using a suitable file format and image information.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items. A file format in this context is understood to be the manner in which the data are arranged and coded in a file. The term corresponds to the normal use in the field of data processing. According to at least one embodiment of the invention, the file format used should have the capability of storing the image data in "layers", i.e. in areas of the file which (at least logically) coherently contains the information necessary for representing an image.

Such file formats are known and are already routinely used, for example in the field of image processing, where a number of layers are used in order to be able to separate image manipulations from one another. A familiar example of such a file format is the format used by the "Photoshop" program by the company Adobe.

Naturally, it is also possible to set up more than two such layers, for example in the case of hybrid instruments which combine three or more different image acquisition technologies and would thus require the combining of three different methods of representation.

The image acquisition is preferably a medical image acquisition which occurs at least a part of a patient's body. Naturally, however, the method according to at least one embodiment of the invention is, in principle, suitable for all fields in which objects are acquired by way of different technologies, for example also in material testing etc.

The term "intended layer format" relates to the fact that the data in the layer are normally present coded and arranged in a manner which is defined by the description of the file format and/or by the program for which this file format was originally developed. As a rule, the data from the image acquisition are also stored in this format so that they can be read, e.g. by the associated program.

The second layer (and possible further layers), too, contains the acquired second image data in the intended layer format which enables this data also to be represented by way of the same program.

However, it may occur that one of the image acquisition systems generates data which do not permit storage in the intended layer format, for example because they contain information which does not have any correspondences in the data structures made possible in the intended layer format.

In at least one embodiment of the invention, therefore, it is provided that the second layer contains the acquired second image data in a separate layer format which meets the formal conditions of the file format. Due to the fact that certain formal conditions are met in spite of a deviation in the layer format, the aim is to ensure that, when a corresponding file is read in, no errors occur and at least the first layer can be represented correctly even if the second layer contains data in a format which cannot be meaningfully represented by the program. By masking the second layer out of the representation at the screen/printer, at least a first layer can be used by the respective program.

It is particularly preferred for the file format to be the DICOM standard since this is a widely used standard in medical imaging and image processing field.

In addition, the possibility of superimposing a further layer, which was originally intended for storing comments and markings by an examining doctor is already implemented in the DICOM standard. The second layer, therefore, preferably corresponds to the DICOM overlay format which implements this functionality.

Due to the preferred use in the medical field, the first image data are preferably MR image data and the second image data are preferably PET image data or SPECT image data, or vice versa.

The first image data can also be CT image data and the second image data can also be PET image data or SPECT image data, or vice versa.

In the method, a mechanism can be implemented in which a user of the hybrid instrument, before generating the combined data by way of the method, has a possibility of selecting the format, wherein he can possibly select between various formats according to at least one embodiment of the invention and furthermore between formats which are not generated in accordance with at least one embodiment of the invention (e.g. separate storage of the various image data).

In a further aspect, at least one embodiment of the invention is directed to a use of a file format and of image data. Everything said with respect to the method according to at least one embodiment of the invention also applies to the use, and vice versa, so that the reference are mutual.

The inventive use of a file format which allows different logical layers of image data to be stored, and of first image data acquired by way of a first image acquisition method and of second image data acquired by way of a second image acquisition method, for generating an image file which contains the acquired first image data in a first logical layer in an intended layer format and contains the acquired second image data in a second logical layer, leads to files which simultaneously contain both (or more) image information items of the hybrid instrument used in a readable format.

As stated, the acquired image data can be medical image data which cover at least a part of a patient's body.

The second layer can contain the acquired second image data in the intended layer format, or in a separate layer format which meets the formal conditions of the file format.

The file format is preferably the DICOM standard, wherein the second layer can correspond to the DICOM overlay format.

The first image data are preferably MR image data and the second image data are preferably PET image data or SPECT image data, or vice versa. The first image data can also be CT image data and the second image data can also be PET image data or SPECT image data, or vice versa.

FIG. 1 shows in a greatly diagrammatic representation a file with image information which has been generated in accordance with the method of an embodiment of the present invention and, respectively, by using a suitable file format and image information. The header area of the file contains general information corresponding to the file format used as is known to the expert in the field. In a first data area of the file, the data relating to the first layer, corresponding to the first acquired image data, are accommodated whilst the data relating to the second layer, corresponding to the second acquired image data, are stored in a second data area.

FIG. 1 additionally shows an optional format area at the beginning of the second storage area in which necessary information on the data format used for representing the second layer can be additionally stored. This format information, in turn, can be formatted in such a manner that it can be read in without errors even by a program which has been designed for reading the data format of the first layer even if the format information or the subsequent second data information cannot be correctly represented by the program.

It is an advantage of an embodiment of the invention that the images are present as "normal", standard-conformal images, for example DICOM overlay images, and, nevertheless, contain the information from both "modalities". It is possible to view only the image of the first layer at any time by simply masking out the overlay, a standard feature of DICOM image viewers.

Existing hardware and software (e.g. workstations, image viewers, post-processing applications) can be continued to be used unchanged and immediately handle the records or files according to the invention as a result of which investments by the user are protected.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for image acquisition, comprising:
   acquiring, by a first imaging method, first image data of an object to be examined;
   acquiring, by a second imaging method, second image data of the object to be examined; and
   generating an image file, a file format of the image file allowing at least a first and a second different logical layer of image data to be stored such that the image file generated contains the acquired first image data in a first logical layer in an intended layer format and the acquired second image data in a second logical layer, the file format being a DICOM standard file format and the second layer corresponding to a DICOM overlay format.

2. The method as claimed in claim 1, wherein the image acquisition is a medical image acquisition and occurs at at least a part of a patient's body.

3. The method as claimed in claim 1, wherein one of the first image data and the second image data are MR image data and another one of one of the first image data and the second image data are at least one of PET image data and SPECT image data.

4. The method as claimed in claim 1, wherein one of the first image data and the second image data are CT image data and another one of one of the first image data and the second image data are at least one of PET image data and SPECT image data.

5. A method, comprising:
   using a file format for image files which allows different logical layers of image data to be stored; and
   generating, using first image data acquired by a first image acquisition method and second image data acquired by a second image acquisition method, an image file which contains the acquired first image data in a first logical layer in an intended layer format and contains the acquired second image data in a second logical layer, the file format being a DICOM standard file format and the second layer corresponding to a DICOM overlay format.

6. The method as claimed in claim 5, wherein the acquired image data are medical image data which cover at least a part of a patient's body.

7. The method as claimed in claim 5, wherein one of the first image data and the second image data are MR image data and another one of one of the first image data and the second image data are at least one of PET image data and SPECT image data.

8. The method as claimed in claim 5, wherein one of the first image data and the second image data are CT image data and another one of one of the first image data and the second image data are at least one of PET image data and SPECT image data.

9. A computer readable medium including program segments for, when executed on a computer device, causing the computer device to implement the method of claim 5.

10. A method for using a file format for image files which allows different logical layers of image data to be generated, the method comprising:
    generating, using first image data acquired by a first image acquisition method and second image data acquired by a second image acquisition method, an image file containing the acquired first image data in a first logical layer in an intended layer format and the acquired second image data in a second different logical layer, the file format being a DICOM standard file format and the second layer corresponding to a DICOM overlay format.

11. A computer readable medium including program segments for, when executed on a computer device, causing the computer device to implement the method of claim 10.

12. A computer readable medium including program segments for, when executed on a computer device, causing the computer device to implement the method of claim 1.

* * * * *